US010959688B2

(12) United States Patent
Brendel et al.

(10) Patent No.: US 10,959,688 B2
(45) Date of Patent: Mar. 30, 2021

(54) X-RAY FLUX REDUCER FOR A PHOTON COUNTING DETECTOR

(71) Applicant: KONINKLIJKE PHILIPS N.V., Eindhoven (NL)

(72) Inventors: Bernhard Johannes Brendel, Norderstedt (DE); Roland Proksa, Neu Wulmstorf (DE); Thomas Koehler, Norderstedt (DE); Ewald Roessl, Ellerau (DE); Heiner Daerr, Hamburg (DE); Michael Grass, Buchholz in der Nordheide (DE); Axel Thran, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 575 days.

(21) Appl. No.: 15/525,079

(22) PCT Filed: Nov. 11, 2015

(86) PCT No.: PCT/IB2015/058691
§ 371 (c)(1),
(2) Date: May 8, 2017

(87) PCT Pub. No.: WO2016/079638
PCT Pub. Date: May 26, 2016

(65) Prior Publication Data
US 2017/0332984 A1 Nov. 23, 2017

Related U.S. Application Data

(60) Provisional application No. 62/082,184, filed on Nov. 20, 2014.

(51) Int. Cl.
*A61B 6/06* (2006.01)
*A61B 6/03* (2006.01)
(Continued)

(52) U.S. Cl.
CPC .............. *A61B 6/06* (2013.01); *A61B 6/032* (2013.01); *A61B 6/035* (2013.01); *A61B 6/4241* (2013.01); *A61B 6/0407* (2013.01)

(58) Field of Classification Search
CPC .......... A61B 6/032; A61B 6/06; A61B 6/035; A61B 6/0407; A61B 6/4241
See application file for complete search history.

(56) References Cited

U.S. PATENT DOCUMENTS 3,715,587 A 2/1973 Burkhalter
4,670,896 A * 6/1987 Klausz ..................... A61B 6/00
378/156

(Continued)

FOREIGN PATENT DOCUMENTS

CN 201088591 Y 7/2008
EP 0146992 A1 7/1985
(Continued)

OTHER PUBLICATIONS

Translation of JP 61-106204 U (Jul. 5, 1986) (Year: 1986).*

*Primary Examiner* — Chih-Cheng Kao
(74) *Attorney, Agent, or Firm* — Larry Liberchuk

(57) ABSTRACT

An imaging system includes a radiation source (108) configured to rotate about an examination region (106) and emit radiation that traverses the examination region. The imaging system further includes an array of radiation sensitive pixels (112) configured to detect radiation traversing the examination region and output a signal indicative of the detected radiation. The array of radiation sensitive pixels is disposed opposite the radiation source, across the examination region. The imaging system further includes a rigid flux filter device (130) disposed in the examination region between the radiation source and the radiation sensitive detector array of photon counting pixels. The rigid flux filter device is configured to filter the radiation traversing the examination (Continued)

region and incident thereon. The radiation leaving the rigid flux filter device has a predetermined flux.

16 Claims, 12 Drawing Sheets

(51) Int. Cl.
*A61B 6/00* (2006.01)
*A61B 6/04* (2006.01)

(56) References Cited

U.S. PATENT DOCUMENTS

| | | |
|---|---|---|
| 6,198,789 B1 | 3/2001 | Dafni |
| 6,744,846 B2 | 6/2004 | Popescu |
| 7,558,364 B2 | 7/2009 | Lin |
| 8,229,059 B2 | 7/2012 | Mukumoto |
| 9,177,682 B2 | 11/2015 | Proksa |
| 9,414,797 B2 | 8/2016 | Flohr |
| 2003/0198319 A1* | 10/2003 | Toth .................. A61B 6/032 378/159 |
| 2005/0089137 A1* | 4/2005 | Toth .................. A61B 6/032 378/19 |
| 2006/0140337 A1* | 6/2006 | Miyazaki ............ A61B 6/032 378/8 |
| 2006/0239396 A1* | 10/2006 | Bruder ............... A61B 6/032 378/4 |
| 2008/0075224 A1 | 3/2008 | Cadwalader |
| 2013/0259191 A1* | 10/2013 | Koehler .............. A61B 6/032 378/19 |
| 2015/0092917 A1* | 4/2015 | Roessl ................ A61B 6/032 378/62 |

FOREIGN PATENT DOCUMENTS

| | | |
|---|---|---|
| JP | S52100991 A | 8/1977 |
| JP | S61106204 U | 7/1986 |
| JP | H9329699 A | 12/1997 |
| JP | 2004321587 A | 11/2004 |
| JP | 2006158690 | 6/2006 |
| JP | 2013236685 A | 11/2013 |
| JP | 2013255850 | 12/2013 |
| RU | 2007148223 | 11/2009 |
| WO | 2013/132361 | 9/2013 |

* cited by examiner

X-RAY FLUX REDUCER FOR A PHOTON COUNTING DETECTOR

CROSS REFERENCE TO RELATED APPLICATIONS

This application is the U.S. National Phase application under 35 U.S.C. § 371 of International Application No. PCT/1132015/058691, filed Nov. 11, 2015, published as WO 2016/079638 on May 26, 2016, which claims the benefit of U.S. Provisional Patent Application No. 62/082,184 filed Nov. 20, 2014. These applications are hereby incorporated by reference herein.

FIELD OF THE INVENTION

The following generally relates to controlling an x-ray flux incident on a photon counting detector of an imaging system, and is described with particular application to computed tomography (CT). However, the following is also amenable to flat panel, x-ray, radiotherapy and/or other imaging applications.

BACKGROUND OF THE INVENTION

A computed tomography scanner includes an x-ray tube that emits an x-ray beam. A portion of the x-ray beam traverses a subject or object located in a field of view of an examination region and is attenuated as a function of the radio density of the subject or object. Another sub-portion of the x-ray beam traverses the field of view of the examination region without traversing the subject or object. A detector array detects the radiation traversing the field of view and produces a signal indicative thereof. A reconstructor reconstructs the signal, producing volumetric image data.

A beam shaper has been positioned in the path of the x-ray beam between the x-ray tube and the examination region. The beam shaper has been referred to as a bowtie filter as its general physical shape resembles a bowtie. The beam shaper is shaped so as to attenuate the beam to a greater degree at a periphery of the beam. This makes the beam shaper well-suited for reducing the flux at the periphery in connection with direct conversion photon counting detectors, which suffer from insufficient count rate capabilities at the higher flux rates.

Unfortunately, for objects or portions of a subject (e.g., the extremities like the legs and arms) with no (or low) attenuating structure between attenuating structures (e.g., the space between the legs), the beam shaper is not well-suited for direct conversion photon counting detectors. This is because, for example, the beam shaper does not reduce the flux at this more central region enough. As a result, some centrally located detector elements of the detector array may receive and detect excessive flux, which can degrade image quality in the reconstructed volumetric image data.

This can be seen in FIG. 10 in connection with objects 1002 and 1004 separated by a gap 1006. In FIG. 10, an emitted beam 1008 is filtered by a beam shaper 1010, which is thicker at peripheral regions 1012 and thinner at a central region 1014, producing a filtered beam 1016, which is filtered to a greater degree at peripheral regions 1018 and to a lesser degree at a central region 1020. A region 1022 of a detector array 1024, which is proximate to the gap 1006, represents a region of a detector array 1024 which receives excessive flux.

SUMMARY OF THE INVENTION

In one aspect, an imaging system includes a radiation source configured to rotate about an examination region and emit radiation that traverses the examination region. The imaging system further includes an array of radiation sensitive pixels configured to detect radiation traversing the examination region and output a signal indicative of the detected radiation. The array of radiation sensitive pixels is disposed opposite the radiation source, across the examination region. The imaging system further includes a rigid flux filter device disposed in the examination region between the radiation source and the radiation sensitive detector array. The rigid flux filter device is configured to filter the radiation traversing the examination region and incident thereon. The radiation leaving the rigid flux filter device has a predetermined flux.

In another aspect, a method includes rotating a radiation source about an examination region. The radiation source emits radiation that traverses the examination region. The method further includes filtering the radiation that traverses the examination region with a rigid flux filter device disposed in the examination region. The method further includes detecting, with detector pixels located opposite the radiation source, across from the examination region, radiation traversing the rigid flux filter device and generating a signal indicative thereof.

In yet another aspect, a rigid flux filter device is configured to be disposed in an examination region between a radiation source and a radiation sensitive detector array of photon counting pixels, wherein the rigid flux filter device is configured to filter the radiation traversing the examination region and incident thereon, and wherein the radiation leaving the rigid flux filter device has a predetermined flux. The rigid flux filter device includes at least one of a polytetrafluoroethylene material or aluminum and having a thickness corresponding to a given radiation source voltage and a give radiation source current.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
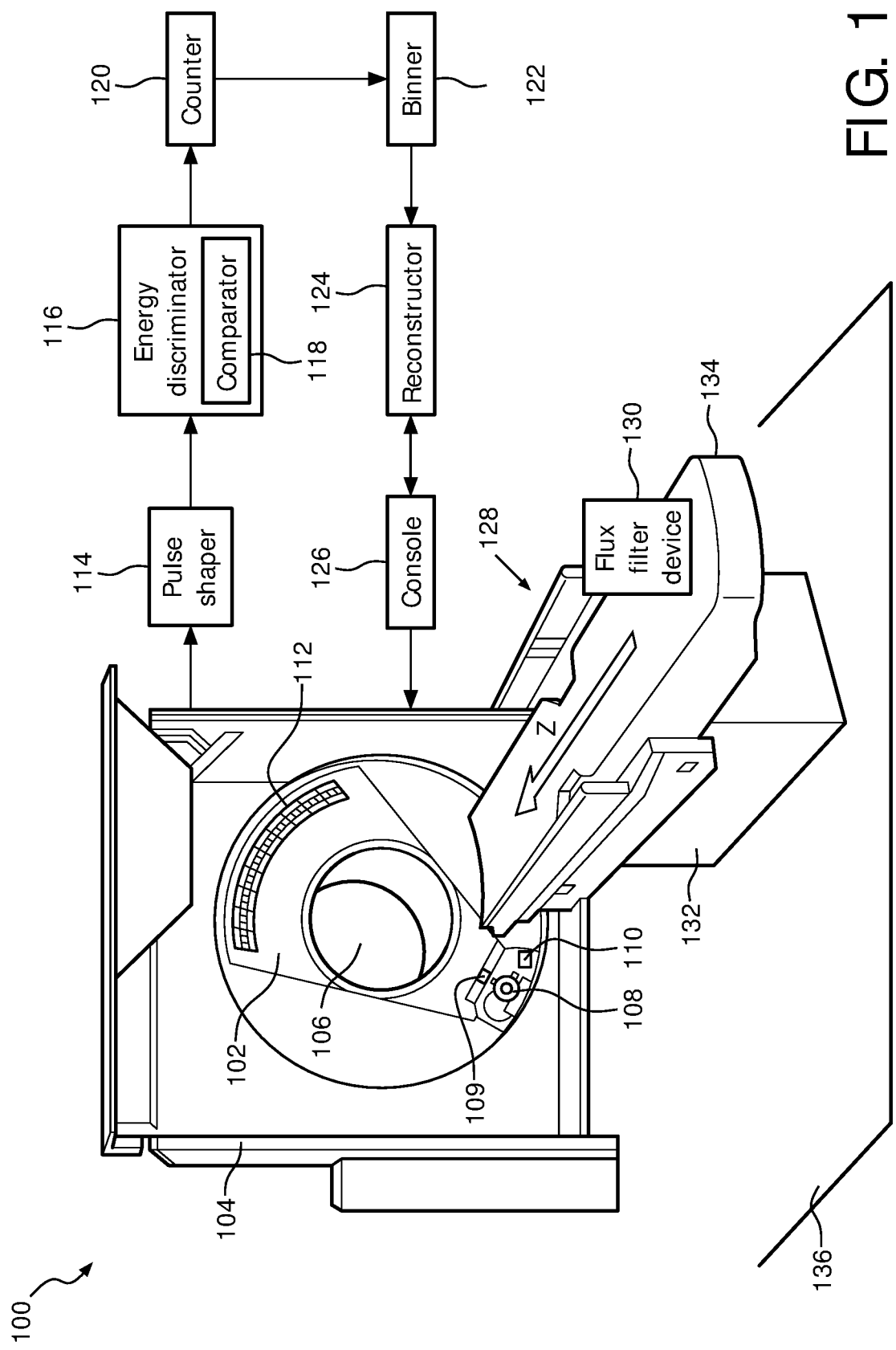
FIG. 1 schematically illustrates an example imaging system with a detector array of photon counting detector pixels in connection with a flux filter device.

FIG. 1 schematically illustrates an example imaging system 100, such as a computed tomography (CT) scanner. The imaging system 100 includes a rotating gantry 102 and a stationary gantry 104. The rotating gantry 102 is rotatably supported by the stationary gantry 104. The rotating gantry 102 is configured to rotate around an examination region 106 about a longitudinal or z-axis.

The imaging system 100 further includes a radiation source 108, such as an x-ray tube, that is rotatably supported by the rotating gantry 102. The radiation source 108 rotates with the rotating gantry 102 around the examination region 106 and is configured to emit radiation that traverses the examination region 106. The imaging system 100 further includes a radiation source controller 110. The radiation source controller 110 is configured to modulate radiation emission. For this, the radiation controller 110 can change the heating current of the cathode, the voltage supplied to the radiation source 108, control a grid switch, which allows or inhibits electrons to flow, move a physical filter into and out of the radiation beam, etc.

The imaging system 100 further includes a beam shaper 109. The beam shaper 109 is disposed in a path of the x-ray beam between the radiation source 108 and the examination region 106. The beam shaper 109 is shaped so as to attenuate the beam to a greater degree at a periphery of the beam. This makes the beam shaper well-suited for reducing the flux at the periphery in connection with direct conversion photon counting detectors, which suffer from insufficient count rate capabilities at the higher flux rates. An example of the beam shaper 109 is a bowtie filter, which has a shape that resembles a bowtie.

The imaging system 100 further includes an array of radiation sensitive pixels 112 arranged along the z-axis direction. The pixels 112 are located opposite the radiation source 108, across the examination region 106, detect radiation traversing the examination region 106, and generate signals indicative of the detected radiation. In the illustrated example, the pixels 112 include direct conversion photon counting detector pixels. With such pixels, a generated signal will include an electrical current or voltage having a peak amplitude or a peak height that is indicative of the energy of a detected photon. The direct conversion photon counting detector pixels may include any suitable direct conversion material such as CdTe, CdZnTe, Si, Ge, GaAs or other direct conversion material.

The imaging system 100 further includes a pulse shaper 114 that processes the electrical signal output by the detector pixels 112 and generates a pulse such as voltage or other pulse indicative of the energy of the detected photon. The imaging system 100 further may include an energy discriminator 116 that energy discriminates the pulse. In the illustrated example, the energy discriminator 116 includes at least one comparator 118, which compares the amplitude of the pulse with at least one energy threshold that corresponds to an energy of interest. The comparator 118 produces an output signal indicative of whether the energy of a detected photon is above or below the threshold.

The imaging system 100 further includes a counter 120 that increments (or decrements) a count value for each threshold. For instance, when the output of the comparator 118 for a particular threshold indicates that the amplitude of the pulse exceeds the corresponding threshold, the count value for that threshold is incremented. The imaging system 100 may further include a binner 122 that assigns the counted pulses to energy bins, which correspond to different energy ranges. For example, a bin may be defined for the energy range between two thresholds. With this example, the binner 122 would assign a photon resulting in a count for the lower threshold but not for higher threshold to the bin defined for the energy range between two thresholds.

The imaging system 100 further includes a reconstructor 124 that reconstructs the binned data using a spectral and/or conventional reconstruction algorithm and generates spectral and/or conventional volumetric image data. The imaging system 100 further includes a computing system that serves as an operator console 126, and includes an output device such as a display and an input device such as a keyboard, mouse, and/or the like. Software resident on the console 126 controls an operation of the system 100, controlling modulation of the tube current in response to the selected scan protocol.

The imaging system 100 further includes a subject support 128 with a base 132 and a tabletop 134. The tabletop 134 is moveably affixed to the base 132 and is configured to translate horizontally in and out of the examination region 106 before, during and after scanning for patient loading, patient scanning and patient unloading. The base 132 is affixed to or rests on a floor 136 in an examination room. The base 132 is configured to move vertically up and down and hence move the tabletop 134 up and down, for example, for loading and unloading a patient and for positioning the patient at a suitable height for scanning, for example, based on the region to be scanned, the iso-center of the scan field of view, and/or otherwise.

A flux filter device 130 is provided for scanning a portion of an object or subject that includes no structure or a low attenuating structure between attenuating structures. For such scanning, the flux filter device 130 is configured to at least attenuate radiation traversing towards an inner region of detector pixels of the array of radiation sensitive pixels 112 (which corresponds to the no structure or low attenuating structure) so that the radiation exiting the flux filter device 130 and incident on inner region of detector pixels has a flux within a predetermined flux range. Generally, the flux filter device 130 is configured to uniformly attenuate the radiation across the radiation beam.

Turning briefly to FIGS. 2, 3, 4, 5, 6, 7 and 8, non-limiting examples of the flux filter device 130 are illustrated.

Figure 2:
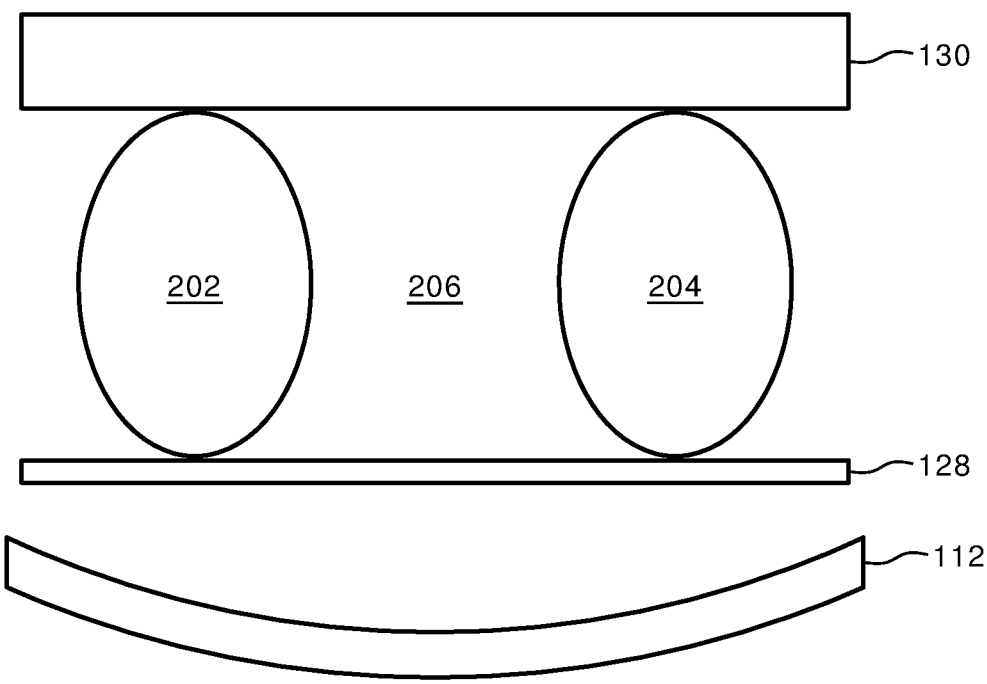
FIG. 2 schematically illustrates an example of a flux filter device.
Figure 3:
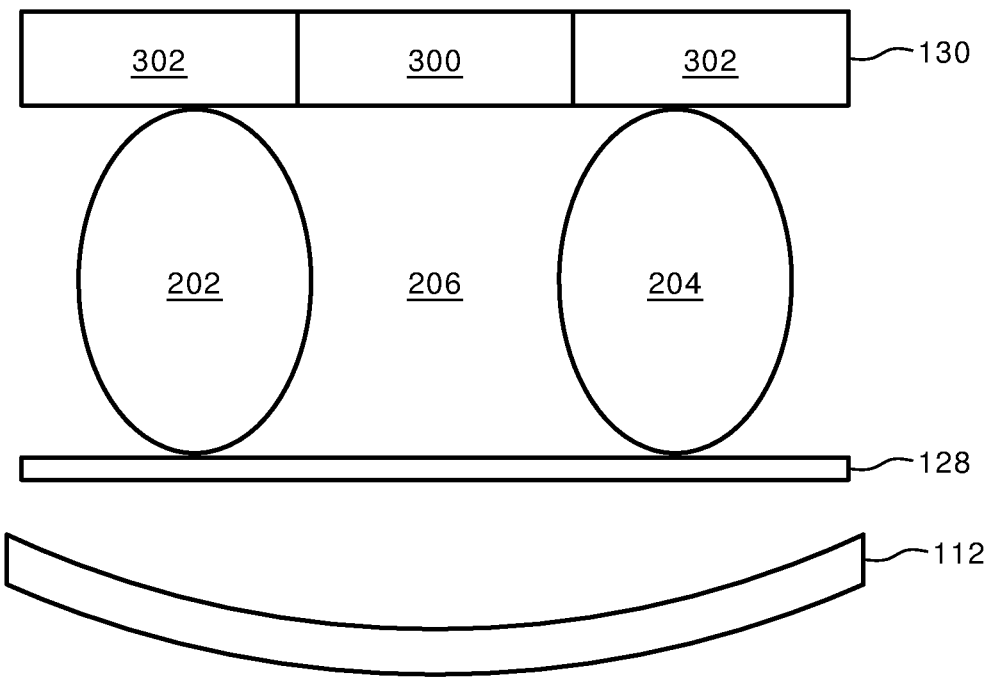
FIG. 3 schematically illustrates another example of a flux filter device.

FIG. 2 shows an embodiment in which the flux filter device 130 is placed and rests on structures 202 and 204 (e.g., the legs) with an air gap 206 in between the structures 202 and 204. In this example, the filter device 130 attenuates radiation uniformly across the structures 202 and 204 and the air gap 206. FIG. 3 also shows an embodiment in which the flux filter device 130 is placed on and rests on the structures 202 and 204 with the air gap 206 in between the structures 202 and 204. However, in this example, the filter device 130 includes an inner region 300, which attenuates the radiation traversing the air gap 206 to prevent excessive flux from reaching the detector array 112, and outer regions 302, which only lightly attenuates radiation.

Figure 4:
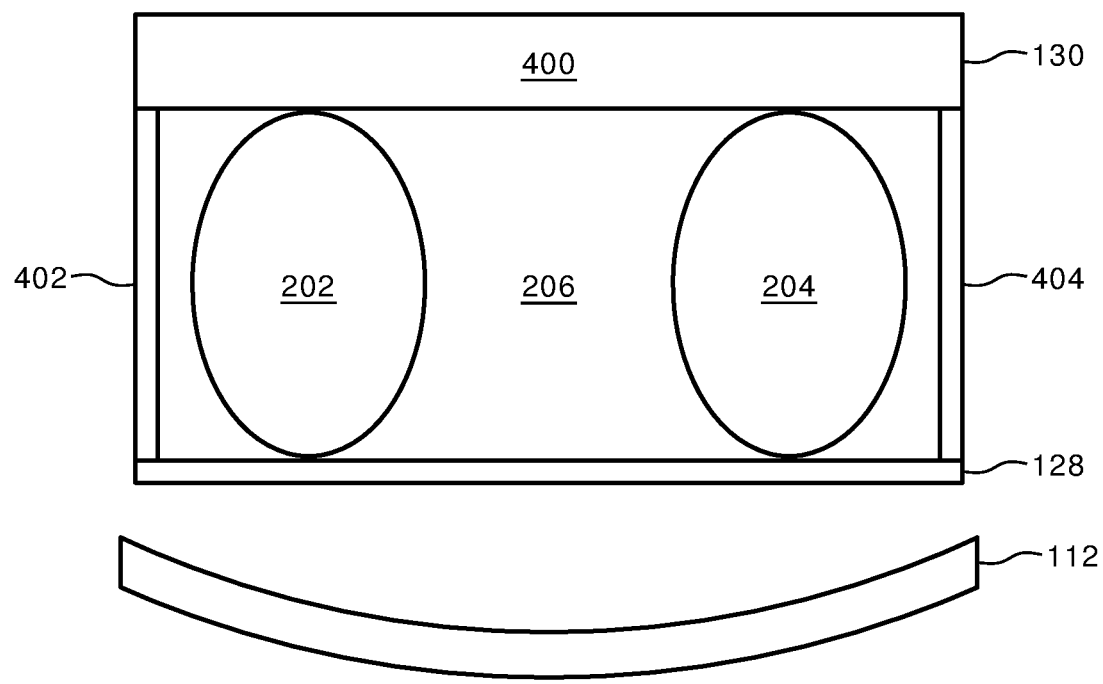
FIG. 4 schematically illustrates another example of a flux filter device.
Figure 5:
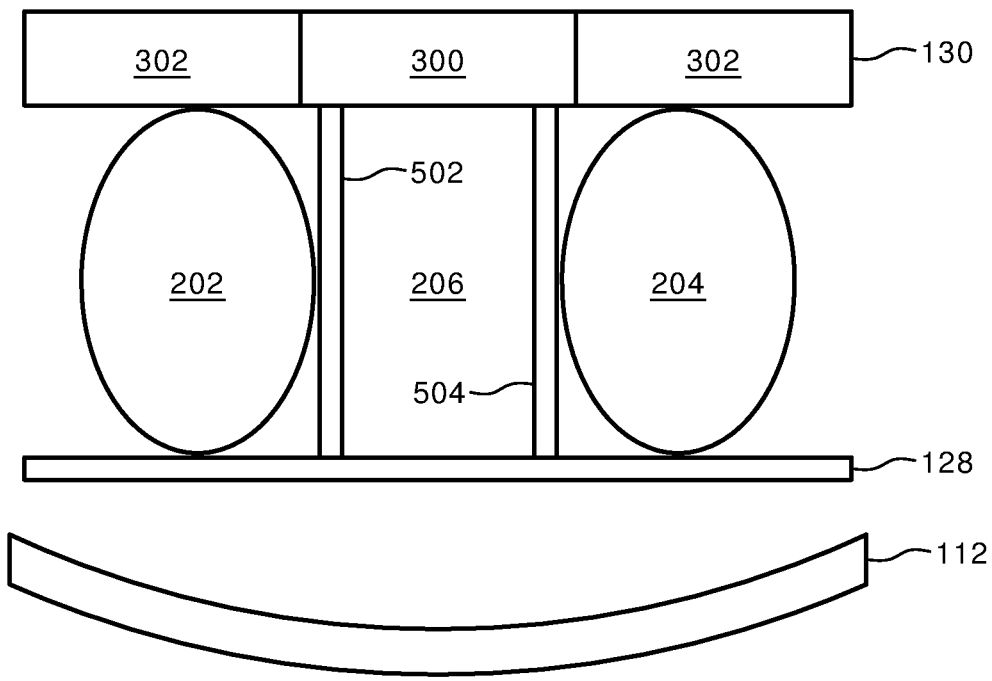
FIG. 5 schematically illustrates another example of a flux filter device.

FIG. 4 is similar to FIG. 2, except that the flux filter device 130 includes a filter portion 400 and brackets 402 and 404, which are configured to rest on the subject support 128 and which hold the filter portion 400 over the structures 202 and 204 and the air gap 206 there between. The brackets 402 and 404 are elongate and rigid, and include a material which only lightly attenuates the x-ray radiation. FIG. 5 is similar to FIG. 3, except that the flux filter device 130 includes brackets 502 and 504, which hold the inner and outer portions 300 and 302 over the structures 202 and 204 and the air gap 206 in there between. Likewise, the brackets 502 and 504 include a material which only lightly attenuates the x-ray radiation.

Figure 6:
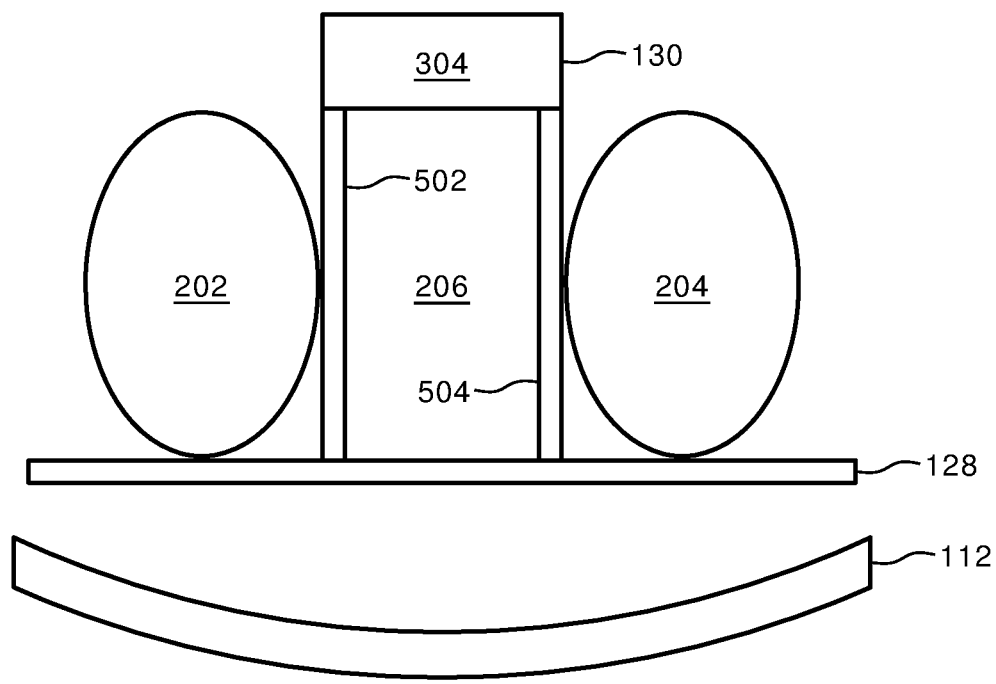
FIG. 6 schematically illustrates another example of a flux filter device.

FIG. 6 is similar to FIG. 5, except that the flux filter device 130 does not include the outer portions 302. With the configurations shown in FIGS. 4-6, it is to be appreciated that the flux filter device 130 may include only a single one of the bracket 402, 404, 502 or 504, or more than two of the brackets 402, 404, 502 or 504. Furthermore, one or more of the brackets 402, 404, 502 or 504 may be configured to be extendable, which would allow adjustment of a height of the flux filter device 130 based on a size of the object being scanned. An example extendable bracket may include a telescoping member, a base member and one or more extension members the affix to the base member, a set of interchangeable and different sized brackets, etc.

Figure 7:
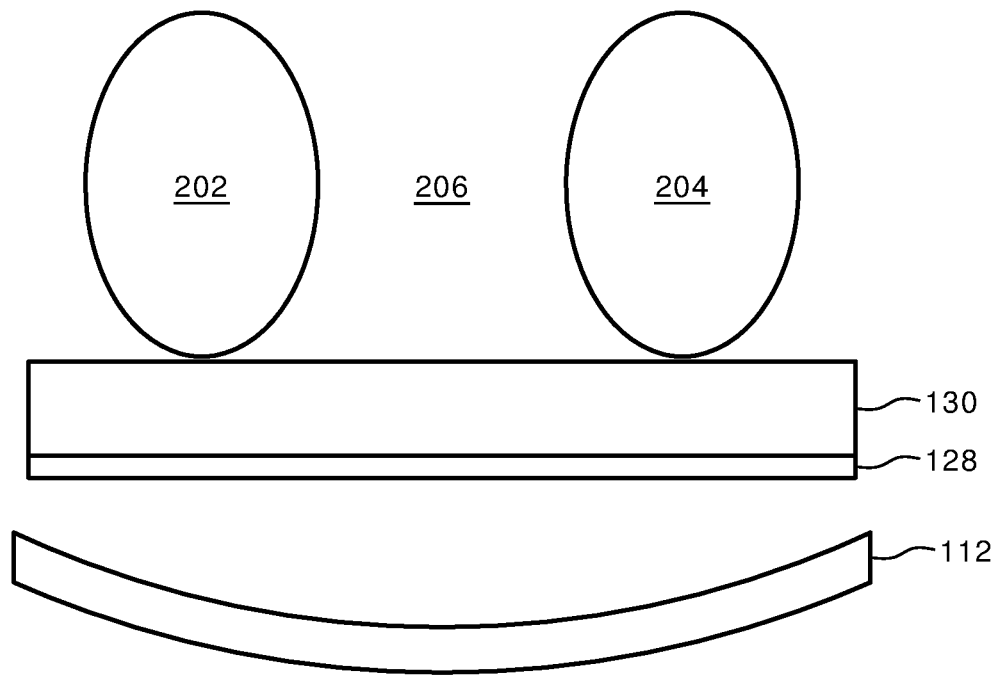
FIG. 7 schematically illustrates another example of a flux filter device.

FIG. 7 shows an example in which the flux filter device 130 of FIG. 2 is placed under the structures 202 and 204 and the air gap 206 between the structures 202 and 204.

With continuing reference to FIGS. 1-7, in one instance, the flux filter device 130 is a rigid structure in that it does not flex and conform to a shape of the object it is placed on. Rather, the flux filter device 130 maintains its shape, regardless of the shape of the object. The illustrated flux filter device 130 includes a material that attenuates radiation so that the photon counting detector pixels 112 receiving non-attenuated radiation or low attenuated radiation are not saturated. The illustrated flux filter device 130 includes a material that attenuates radiation by way of photo-electric absorption and by Compton scattering. A suitable material includes a high atomic weight, Z, (e.g., Z≥13) material that has relatively higher photo-electric absorption than water or typical soft-tissue.

Generally, the flux filter device 130 provides a predetermined compromise between photo-electric absorption and beam hardening. An example of such a material includes Polytetrafluoroethylene (PTFE) which is a synthetic fluoropolymer of tetrafluoroethylene, aluminum (Al) or the like. An example of a suitable PTFE material is Teflon®, which is a product of DuPont Co., USA.

A thickness of the flux filter device 130 depends on scan protocol parameters such as tube voltage (V), tube current (I), beam conditioner (e.g., a pre patient filter) settings (B). A maximal flux of a central detector pixel can be estimated based on a function F(V,B,I) by way of a theoretical physical model of the scanner or a calibration procedure. For the latter, the flux $F_{calib}(V,B,I_{calib})$ on the central detector is measured for all possible V and B settings and one current ($I_{calib}$). For a maximal flux of $F_{Max}$ on the detector for a scan with scan protocol parameters $F_{Scan},B_{Scan},I_{Scan}$, the flux filter device 130 will have a linear absorption $\mu_A$ and thickness $t_A$ that satisfies:

$$F_{max} \geq \frac{I_{Scan}}{I_{Calib}} F_{Calib}(V_{Scan}, B_{Scan}, I_{Calib}) e^{-\mu_A t_A}.$$

A set of flux filter devices 130 can be created for one or more different combinations of the scan protocol parameters $F_{Scan},B_{Scan}, I_{Scan}$. The particular flux filter device 130 for a scan can then be selected by the clinician from the set of flux filter devices 130 that includes a flux filter device 130 for one or more different combinations of the scan protocol parameters $F_{Scan},B_{Scan}, I_{Scan}$. In one instance, a user selects a protocol and the console 126 presents information that identifies a suitable flux filter device 130 for the protocol. The flux filter device 130, depending on the configuration, can be placed on the object or subject (FIG. 2) to cover the structures and any no or low attenuation region between the structures, or on the subject support 128 (FIG. 3) to cover the structures and any no or low attenuation region between the structures.

Figure 8:
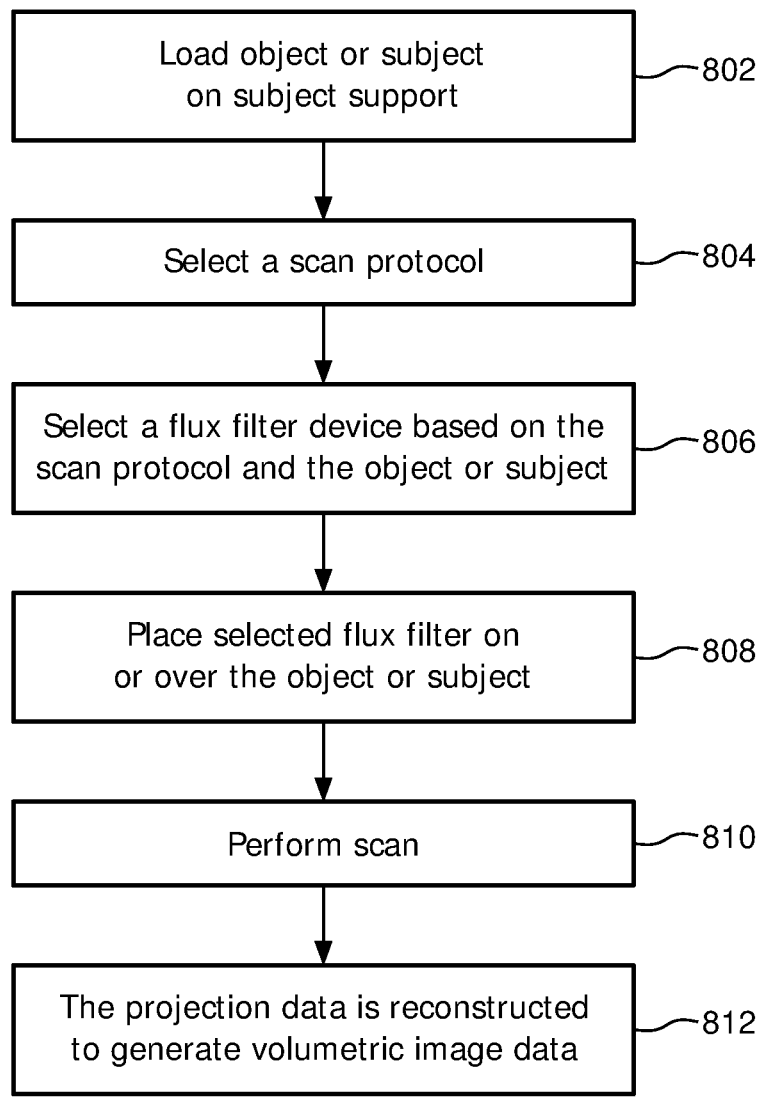
FIG. 8 illustrates a method for employing the flux filter device with the example imaging system.

FIG. 8 illustrates a method in accordance with an embodiment described herein.

It is to be appreciated that the ordering of the below acts is for explanatory purposes and not limiting. As such, other orderings are also contemplated herein. In addition, one or more of the acts may be omitted and/or one or more other acts may be included.

At 802, an object or subject is loaded onto the subject support.

At 804, a scan protocol is selected at a console.

At 806, a flux filter device is selected based on the scan protocol parameters and the object or subject.

At 808, the selected flux filter device is placed on or over the object or subject.

At 810, the scan is performed.

At 812, the projection data is reconstructed to generate volumetric image data.

Figure 9:
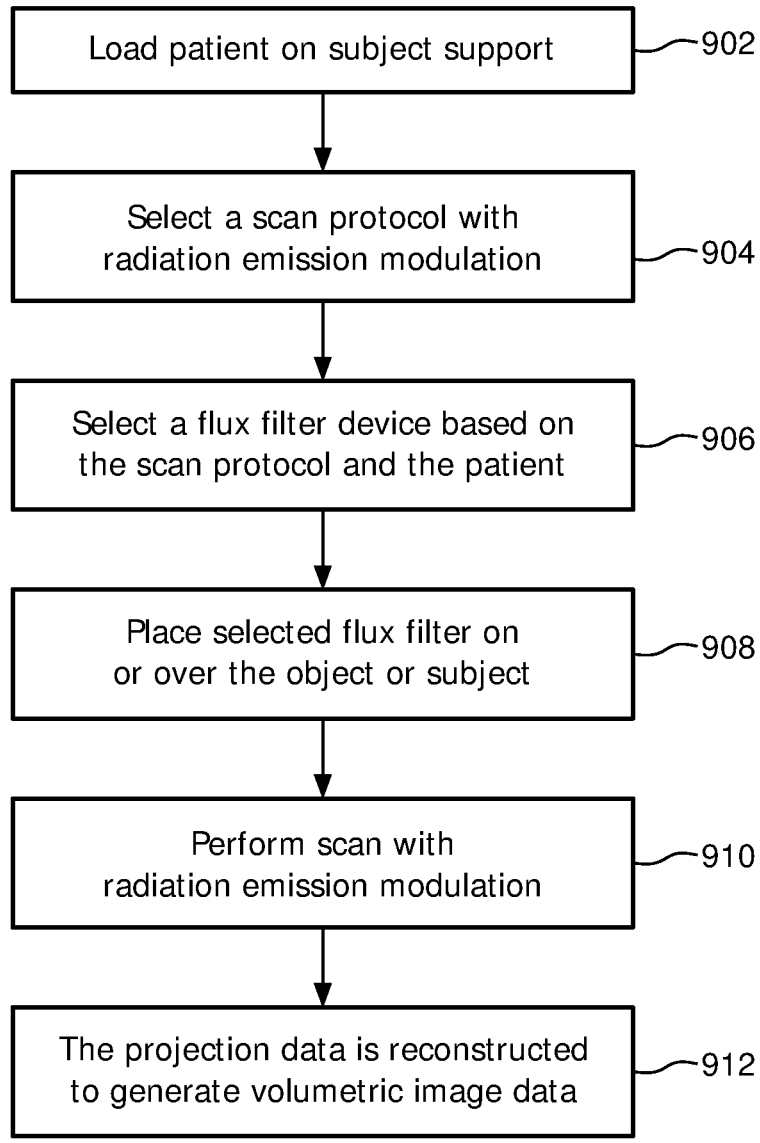
FIG. 9 illustrates another method for employing the flux filter device with the example imaging system.
Figure 10:
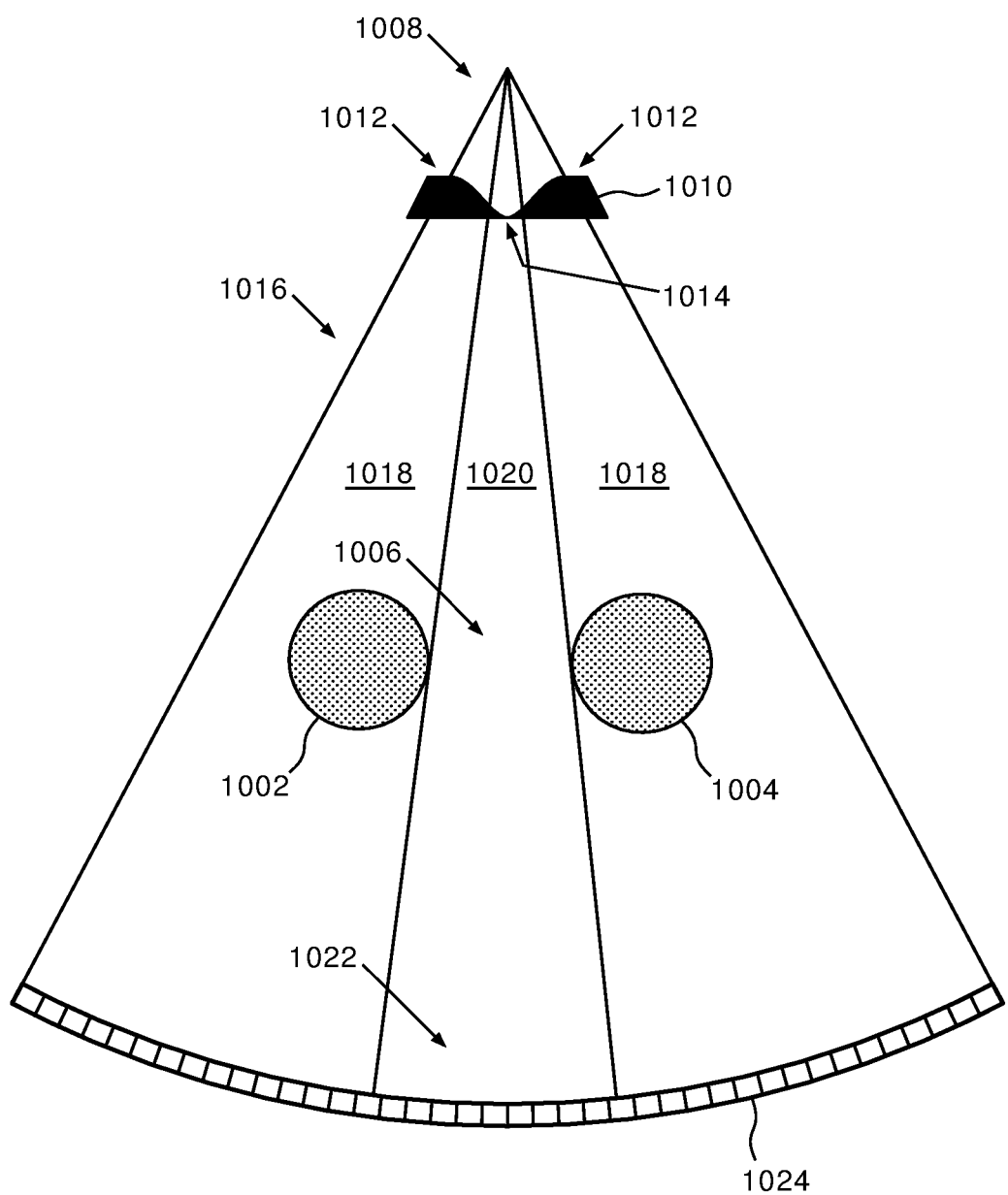
FIG. 10 illustrates an example of a prior art example of a flux filter device.

FIG. 9 illustrates another method in accordance with an embodiment described herein. In this example, the subject is a human or animal patient, and the flux filter device 130 is placed so that the patient is between flux filter device 130 and the subject support 128, e.g., as shown in FIGS. 2-6.

It is to be appreciated that the ordering of the below acts is for explanatory purposes and not limiting. As such, other orderings are also contemplated herein. In addition, one or more of the acts may be omitted and/or one or more other acts may be included.

At 902, a patient is positioned onto the subject support 128.

At 904, a scan protocol is selected at the console 126. In this example, the selected scan protocol causes the radiation source controller 110 to modulate radiation emission with a modulation pattern that modules the radiation emission between at least a first flux and a second different flux. As described next, such modulation may be dependent on the radiation source 108 angle.

For example, one modulation pattern will cause the controller 110 to modulate the radiation emission so that the flux is lower when the radiation source is rotating from the 3 o'clock position, through the 6 o'clock position at which the radiation source 108 is under a portion of the subject support disposed in the examination region 106, to the 9 o'clock position (or from the 9 o'clock position, through the 6 o'clock position, to the 3 o'clock position if the system rotates counter-clockwise).

Furthermore, this modulation pattern will cause the controller 110 to modulate the radiation emission so that the flux is higher when the radiation source is rotating from the 9 o'clock position, through the 12 o'clock position at which the radiation source 108 is opposite the portion of the subject support disposed in the examination region 106, to the 3 o'clock position (or from the 3 o'clock position, through the 12 o'clock position, to the 9 o'clock position).

The flux can be modulated through controlling a heating current in a cathode of the radiation source 108. In another instance, the lower of the two fluxes is no flux, e.g., using a grid switch, a physical filter, etc. to inhibit radiation from traversing the examination region 106.

At 906, a flux filter device 130 is selected from a set of flux filter devices 130 based on the scan protocol parameters.

At 908, the selected flux filter device 130 is placed on or over the patient, as described herein and/or otherwise.

At 910, the patient is scanned using the modulation pattern.

For example, during the scan, the radiation source controller 110 modulates the radiation emission so that the flux is a lower flux as the radiation source rotates from the 3 o'clock position, through the 6 o'clock position, to the 9 o'clock position (or from the 9 o'clock position, through the 6 o'clock position, to the 3 o'clock position for a counter clockwise rotation), and a higher flux as the radiation source rotates from the 9 o'clock position, through the 12 o'clock, to the 3 o'clock position (or from the 3 o'clock position, through the 12 o'clock position, to the 9 o'clock position for a counter clockwise rotation).

At 912, the projection data is reconstructed to generate volumetric image data.

In FIG. 9, the filter device 130 is placed opposite the subject support 128 with the objects 202 and 204 between the filter device 130 and the subject support 128 as shown in FIGS. 2-6. In an embodiment in which the filter device 130 is placed between the objects 202 and 204 and the subject support 128, as shown in FIG. 7, the flux is modulated so the flux is at the lower level as the radiation source rotates from the 9 o'clock position, through the 12 o'clock, to the 3 o'clock position and at the higher flux as the radiation source rotates from the 3 o'clock position, through the 6 o'clock position, to the 9 o'clock position. In general, the particular modulation pattern utilized is selected so that it attenuates the flux before it passes the patient rather than afterwards because any attenuation before the patient implies a reduction of x-ray dose, whereas an attenuation afterwards imply a waste of dose.

More particularly, by modulating the radiation emission as such, radiation dose to the patient is reduced while the radiation source 108 is at a location in which radiation traversing the object or subject is subsequently filtered, relative to the location in which the radiation is filtered prior to traversing the patient. Where the radiation source 108 is at a location at which radiation is filtered prior to traversing the patient, the flux seen by the detector is reduced and the patient dose is lowered. Where the radiation source 108 is at a location at which radiation traversing the object or subject is subsequently filtered, the flux seen by the detector is reduced but without the reduction in patient dose, which results in wasted dose in that the x-ray traversing a patient are filtered and do not contribute to generation of the volumetric image data. The above modulation pattern reduces this dose inefficiency, which includes dose to the patient that is not utilized to generate the volumetric image data.

Figure 11:
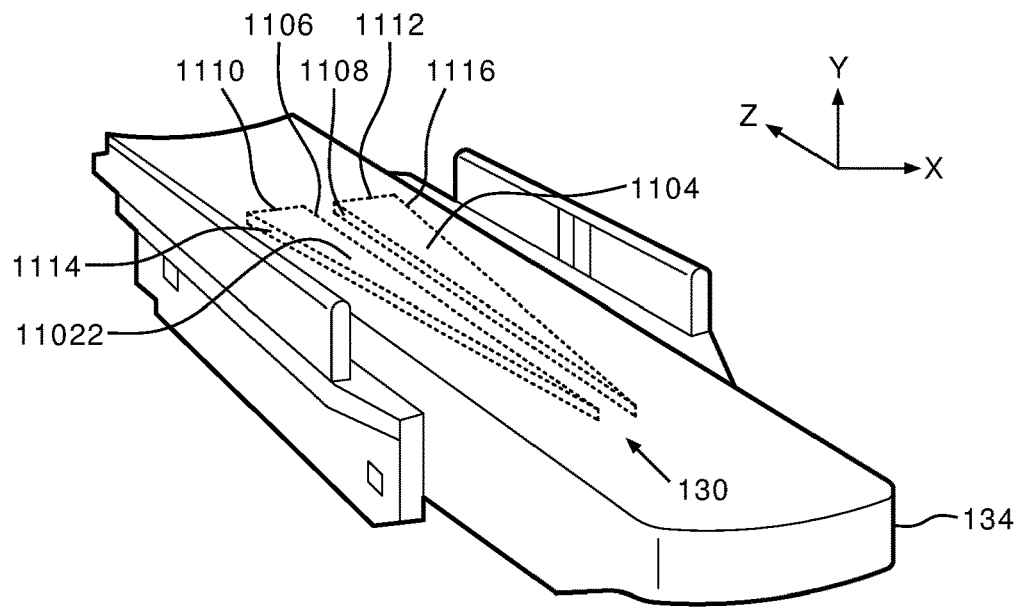
FIG. 11 schematically illustrates a perspective view of an example of a flux filter device configured to be disposed in a tabletop of the subject support.
Figure 12:
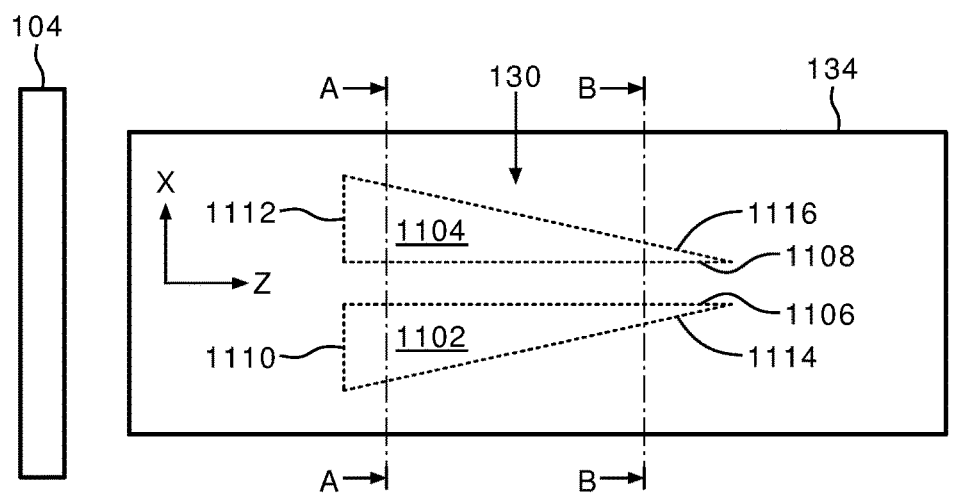
FIG. 12 schematically illustrates a top down view of the example flux filter device of FIG. 11.
Figures 13, 14:
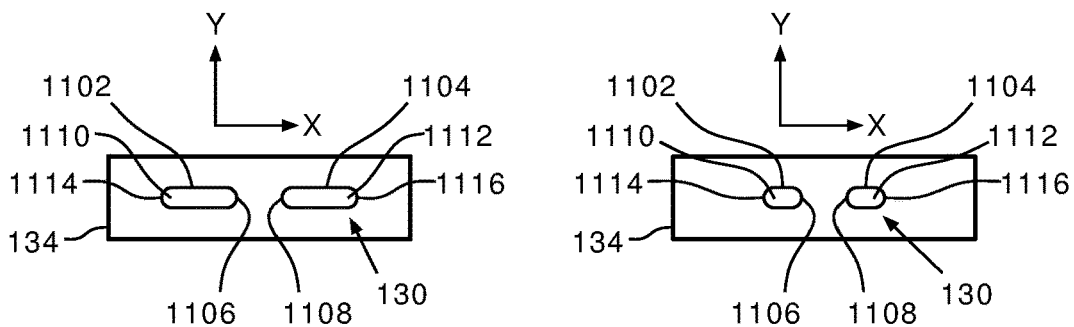
FIG. 13 schematically illustrates a first cross-sectional view of the example flux filter device of FIG. 11.
FIG. 14 schematically illustrates a second cross-sectional view of the example flux filter device of FIG. 11.

FIGS. 11-14 illustrates an embodiment in which the flux filter device 130 removably installs within or inside of the tabletop 134. FIG. 11 shows a perspective view of the flux filter device 130. FIG. 12 shows a top down view of the flux filter device 130. FIG. 13 shows a first cross-sectional view of the flux filter device 130 along line A-A of FIG. 12. FIG. 14 shows a second cross-sectional view of the flux filter device 130 along line B-B of FIG. 12.

The flux filter device 130 includes one or more flux reducing elements. For sake of clarity and brevity, two flux reducing elements 1102 and 1104 are shown in this example. Each flux reducing element 1102 (or 1104) has a shape of a right triangle, with a first side 1106 (or 1108) that extends along the z-axis, a second side 1110 (or 1112) that extends along an x-axis perpendicular from the first side 1106 (or 1108), and a third side 1114 (or 1116) which is opposite the right angle formed at the intersection of the first and second sides 1106 (or 1108) and 1110 (or 1112). Other shapes are also contemplated herein.

The flux reducing elements 1102 and 1104 are aligned in a cavity of the tabletop 134 with respect to each other in an x/z plane with the first sides 1106 and 1108 facing each other. A position of the one or more flux reducing elements 1102 and 1104 is adjustable manually and/or by external control in the x and/or z directions. Based on a scout and/or other scan, the one or more flux reducing elements 1102 and 1104 are positioned so that they add x-ray absorbing material to regions with low absorption and/or no absorption.

Figure 15:
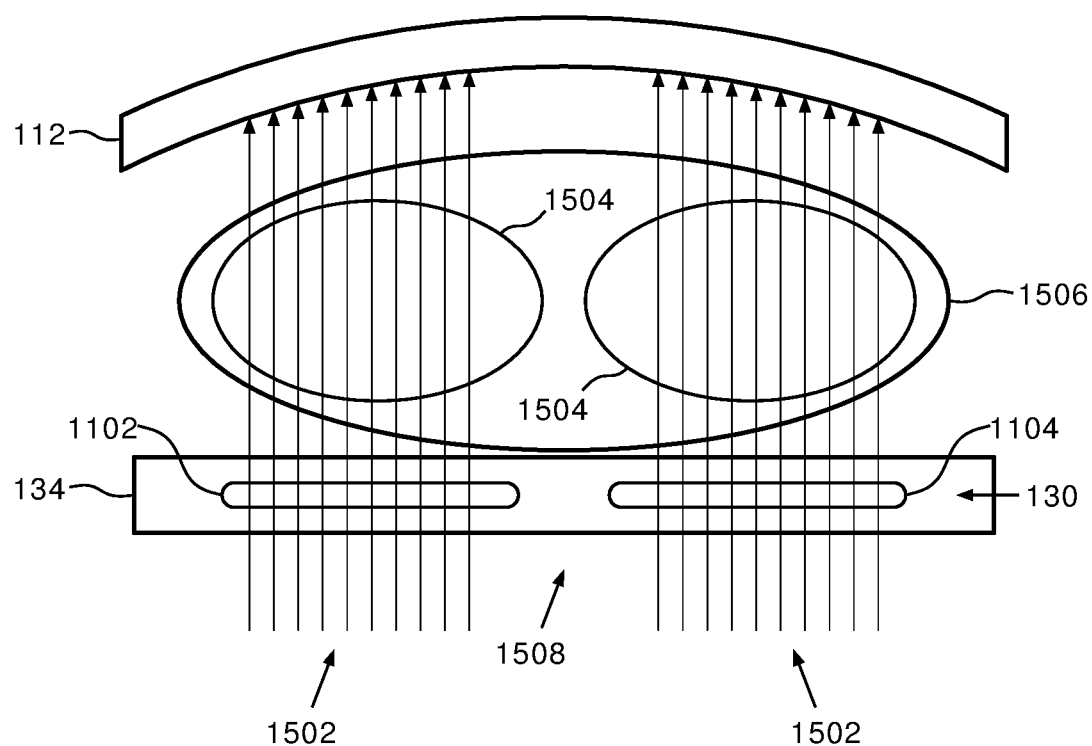
FIG. 15 schematically illustrates the example flux filter device of FIG. 11 in connection with scanning the thorax.
Figure 16:
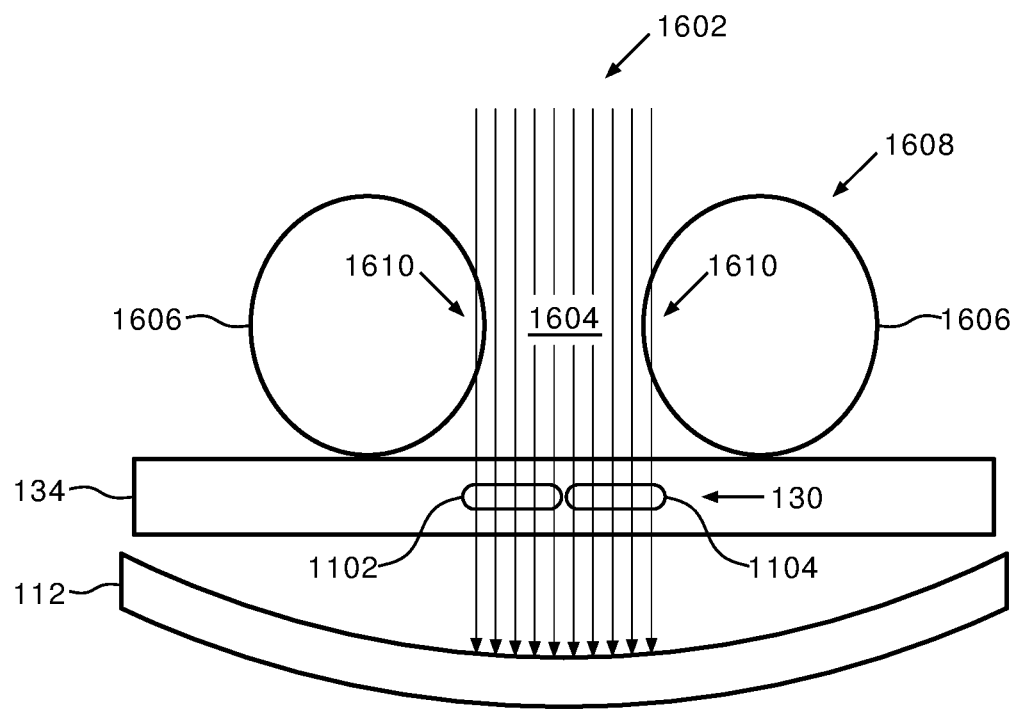
FIG. 16 schematically illustrates the example flux filter device of FIG. 11 in connection with scanning the lower extremities.

FIG. 15 schematically illustrates an example in which the one or more flux reducing elements 1102 and 1104 attenuate x-rays 1502 traversing lungs 1504 (i.e., low absorption) of a patient 1506. FIG. 16 schematically illustrates an example in which the one or more flux reducing elements 1102 and 1104 attenuate x-rays 1602 traversing an empty space 1604 between legs 1606 (i.e., no absorption) of a patient 1608 and/or an inner periphery 1610 of the legs 1606 (i.e., low absorption). X-rays traversing higher attenuating portions of the patients 1506 and 1608 are not shown for sake of clarity.

For a scan covering the thorax and at least a sub-portion of the lower extremities, the one or more flux reducing elements 1102 and 1104 are moved at least in the x-direction from a position in which there is a non-zero gap 1508 between the one or more flux reducing elements 1102 and 1104 for scanning the lungs (FIG. 15) to a different position in which the one or more flux reducing elements 1102 and 1104 abut and form a continuous additional x-ray absorbing region between the legs for scanning the lower extremities (FIG. 16). The movement can be continuous or discrete. Moving the flux-reducing device 130 during the scan is well suited for a scan with a large extent in z-direction, where the flux reducing elements 1102 and 1104 would not perfectly cover the regions of low absorption without such a movement. Otherwise, the flux reducing elements 1102 and 1104 remain stationary with respect to the tabletop 134.

In FIGS. 11-16, the flux filter device 130 is installed so that the first sides 1106 and 1108 are proximate to the rotating gantry 104. This configuration is well suited where the patient is lying on the tabletop 134 with their head proximate and their feet distal to the rotating gantry 104. In a variation, the flux filter device 130 is installed so that the first sides 1106 and 1108 are distal to the rotating gantry 104 to the rotating gantry 104. This configuration is well suited where the patient is lying on the tabletop 134 with their head distal and their feet proximate to the rotating gantry 104. Furthermore, the flux filter device 130 is shown in FIGS. 13-16 with curved sides. It is to be understood that the curvature shown is non-limiting, and the flux filter device 130 may have other radii of curvature, flat sides, irregular sides, and/or other shaped sides.

Figure 17:
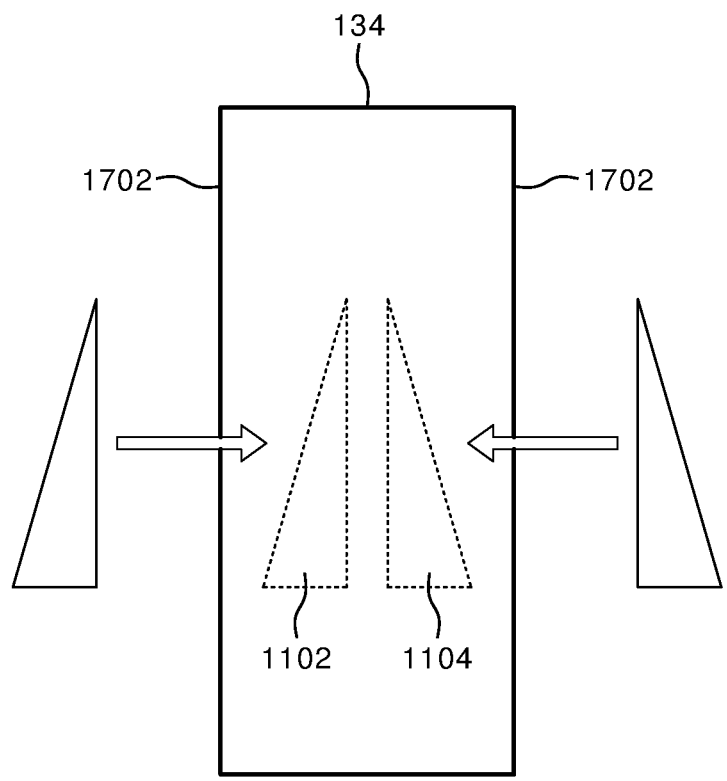
FIG. 17 schematically illustrates an example in which the flux filter device of FIG. 11 is installed and removed from sides of the tabletop.
Figure 18:
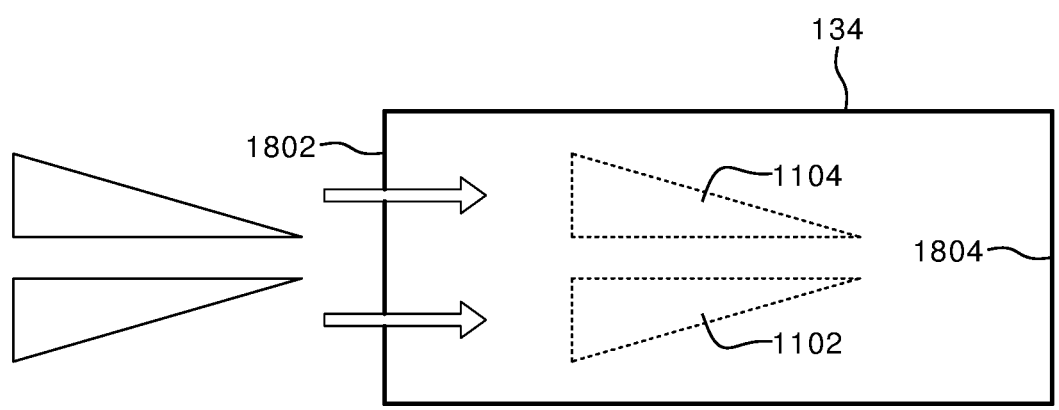
FIG. 18 schematically illustrates an example in which the flux filter device of FIG. 11 is installed and removed from the back of the tabletop.

FIG. 17 schematically illustrates an embodiment in which the one or more flux reducing elements 1102 and 1104 are installed and removed from the tabletop 134 from sides 1702 of the tabletop 134. FIG. 18 schematically illustrates an embodiment in which the one or more flux reducing elements 1102 and 1104 are installed and removed from the tabletop 134 from a back 1802 of the tabletop 134. In another instance, the one or more flux reducing elements 1102 and 1104 can be installed in the tabletop 134 and removed from the tabletop 134 from a front 1804 and/or other region of the tabletop 134. The one or more flux reducing elements 1102 and 1104 are installed and removed through an access.

Figure 19:
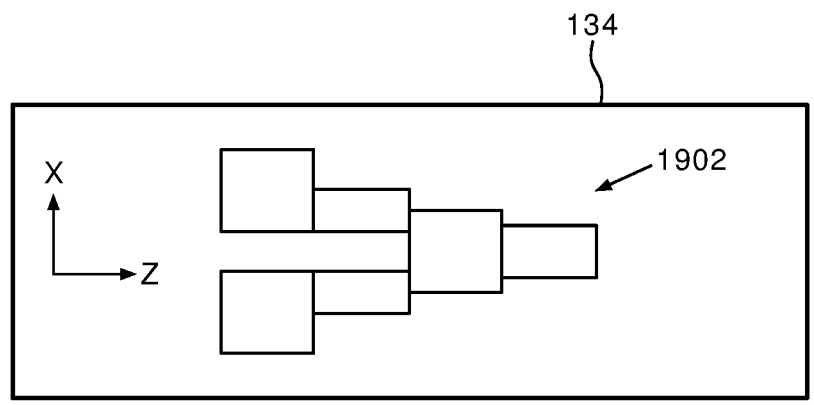
FIG. 19 schematically illustrates a variation of the example flux filter device of FIG. 11.

FIG. 19 shows a variation in which the flux filter device 130 includes a plurality of plates 1902. The plurality of plates 1902 has invariant cross-sections over the z direction that is larger than a size of the beam in the z direction. During a scan, the plurality of plates 1902 can be moved within the tabletop 134 so that the position of the plurality of plates 1902 does not change with respect to a rotating gantry 102. The plurality of plates 1902 can be installed and removed from the tabletop 134 as described in connection with FIGS. 17 and 18 and/or otherwise.

Figure 20:
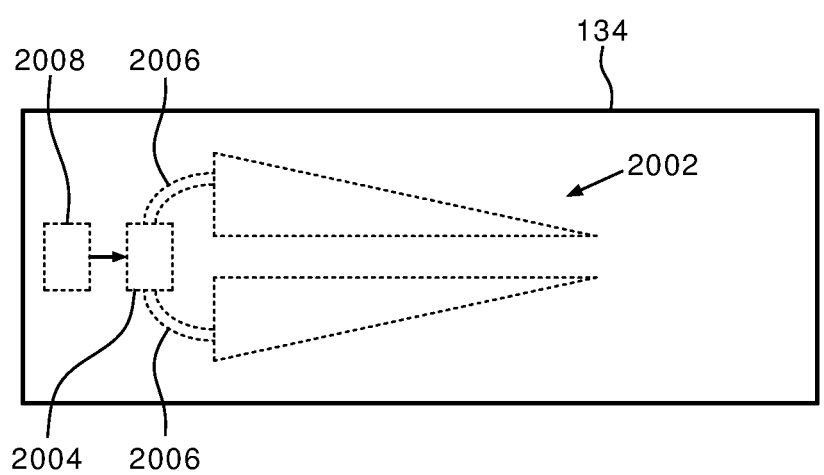
FIG. 20 schematically illustrates another variation of the example flux filter device of FIG. 11.

FIG. 20 shows a variation in which one or more hollow containers 2002 are disposed inside the tabletop 134. In this variation, the one or more hollow containers 2002 can be filled with a highly absorbing gas 2004 (e.g., Xenon) through conduits 2006. The absorption of the one or more hollow containers 2002 can be modified by adjusting a pressure of the gas inside the one or more hollow containers 2002 via a pressure regulator 2008. The gas 2004 and/or hollow containers 2002 may reside in the base 132 of the subject support 128, the stationary gantry 104, a portion of the tabletop 134 that is not irradiated, and/or otherwise.

In a variation of FIG. 20, the one or more hollow containers 2002 may include an expandable and/or a flexible container such as a bag, a balloon, etc. The expandable and/or a flexible container can be used inside and/or outside of the tabletop 134. For example, the expandable and/or a flexible container may be filled (or pre-filled) with the highly absorbing gas 2004 and/or other absorbing gas, and then positioned between extremities outside of the tabletop 134. In this instance, the expandable and/or a flexible container attenuates the radiation traversing the air gaps 206 and 1604 shown in FIGS. 2-6 and 16 to prevent excessive flux from reaching the detector array 112. The expandable and/or a flexible container may be squeezed and held in place via the extremities, a support or holding device, and/or otherwise.

With the configurations of FIGS. 11-20, the tube current can be modulated as described herein to decrease the flux when the additional attenuating material is between the patient 1506 and 1608 and the detector array 112 such that x-rays first traverse the patient 1506 and 1608 and then the additional attenuating material of the flux filter device 130, and to increase the flux when the additional attenuating material is not between the patient 1506 and 1608 and the detector array 112 such that x-rays first traverse the additional attenuating material and then the patient 1506 and 1608. This will facilitate mitigating dose inefficiencies, as described herein.

Figure 21:
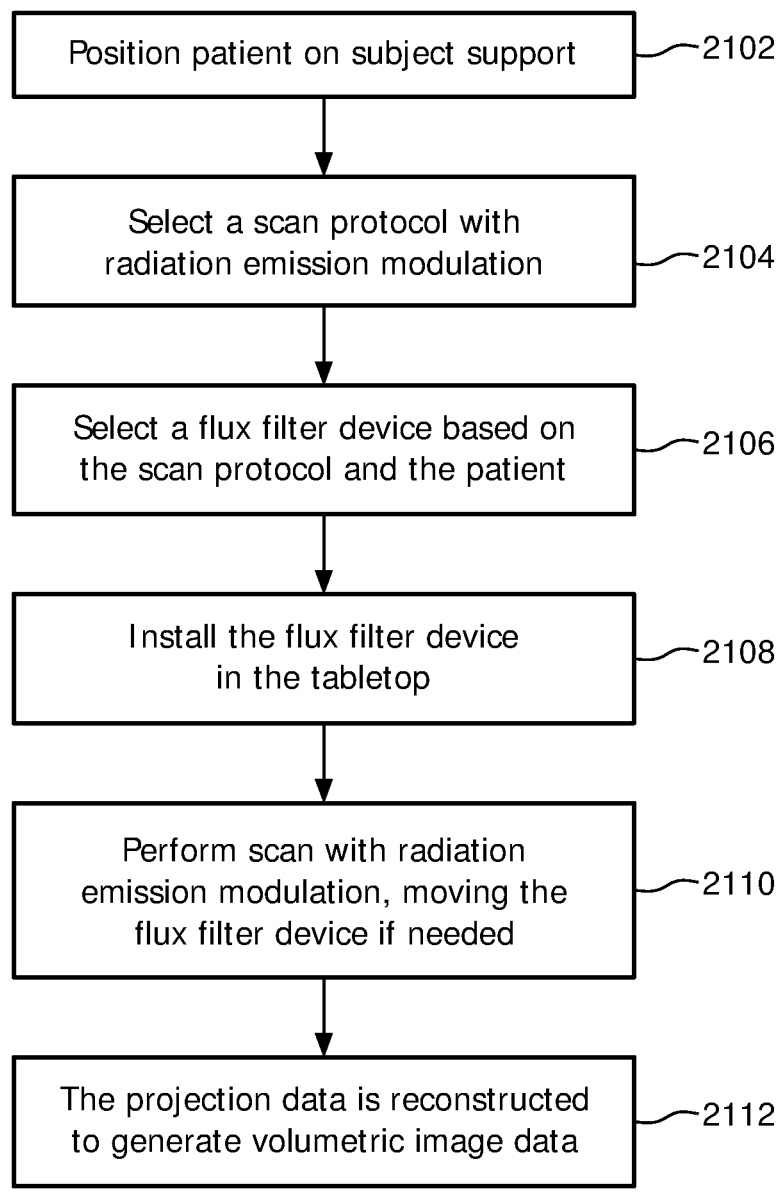
FIG. 21 illustrates method for employing the flux filter device of FIG. 11.

FIG. 21 illustrates another method in accordance with an embodiment described herein.

It is to be appreciated that the ordering of the below acts is for explanatory purposes and not limiting. As such, other orderings are also contemplated herein. In addition, one or more of the acts may be omitted and/or one or more other acts may be included.

At 2102, a patient is positioned on the subject support 128.

At 2104, a scan protocol is selected at the console 126. In this example, the selected scan protocol causes the radiation source controller 110 to modulate radiation emission with a modulation pattern that modules the radiation emission between at least a lower and a higher different flux, depending on the radiation source 108 angle.

At 2106, a flux filter device 130 is selected from a set of flux filter devices 130 based on the scan protocol parameters.

At 2108, the selected flux filter device 130 is moved into position in the tabletop 134. As described herein, this may include moving the physical mechanical devices 1102 and 1104 into position and/or filing the one or more hollow containers 2002 with the highly absorbing gas 2004.

At 2110, the patient is scanned using the modulation pattern and moving the flux filter device 130, if needed.

At 2112, the projection data is reconstructed to generate volumetric image data.

Generally, the different embodiments of the flux filter device 130 described herein can be used with X-ray and CT systems with photon counting detectors to solve the count rate problem. The different embodiments of the flux filter device 130 can be used for medical applications scanning the thorax, extremity, etc. as well as dental and/or non-medical applications such as non-destructive testing, etc.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   an x-ray radiation source configured to rotate about an examination region and emit x-ray radiation that traverses the examination region;
   an array of x-ray radiation sensitive pixels configured to detect x-ray radiation traversing the examination region and output a signal indicative of the detected x-ray radiation, wherein the array of x-ray radiation sensitive pixels is disposed opposite the x-ray radiation source, across the examination region; and
   a rigid flux filter device disposed in the examination region between the x-ray radiation source and the x-ray radiation sensitive detector array of pixels, wherein the flux filter device does not rotate together with the x-ray radiation source and is configured to filter the x-ray radiation traversing the examination region and incident thereon, and wherein the x-ray radiation leaving the flux filter device has a predetermined flux,
   wherein along an axis direction around which the x-ray radiation source rotates, the rigid flux filter device is configured to slide, relative to the examination region, toward the examination region from a location at which the rigid flux filter device is spaced apart from the examination region in the axis direction.

2. The imaging system of claim 1, wherein the rigid flux filter device includes an inner region with first attenuation characteristics, a first outer region with second attenuation characteristics, and a second outer region,
wherein the inner region is disposed between the first and second outer regions in a plan view, and
wherein the inner region that is disposed between the first and second outer regions in the plan view attenuates the x-ray radiation to a greater degree than each of the first and second outer regions.

3. The imaging system of claim 1, wherein the rigid flux filter device includes at least one of a synthetic fluoropolymer of tetrafluoroethylene material or aluminum.

4. The imaging system of claim 1, wherein the x-ray radiation sensitive detector array includes photon counting pixels.

5. The imaging system of claim 1, wherein the rigid flux filter device has a thickness corresponding to a given x-ray radiation source voltage and a given x-ray radiation source current.

6. The imaging system of claim 5, wherein the rigid flux filter device is one rigid flux filter device from a set of flux filter devices, each having a thickness corresponding to a different combination of different given x-ray radiation source voltage and x-ray radiation source current setting.

7. The imaging system of claim 1, wherein the rigid flux filter device at least filters x-ray radiation directed towards an inner region of detector pixels of the array of x-ray radiation sensitive pixels based on a predetermined flux value.

8. The imaging system of claim 1, further comprising:
a source controller configured to modulate an x-ray radiation source current of the x-ray radiation source between at least a first flux and a second different flux.

9. The imaging system of claim 8, wherein the source controller employs a predetermined pattern that modulates the x-ray radiation source current based on a current angle of the x-ray radiation source with respect to the examination region.

10. The imaging system of claim 1, further comprising:
a source controller configured to maintain a same flux throughout a scan.

11. The imaging system of claim 1, further comprising:
a subject support, and wherein the rigid flux filter device includes a filter and at least one bracket configured to rest on the subject support and support the filter over the subject support.

12. The imaging system of claim 1, further comprising:
a subject support with a tabletop having a long axis along a z-direction, wherein the rigid flux filter device is disposed inside of the tabletop.

13. The imaging system of claim 12, wherein the rigid flux filter device includes a flux reducing element that increases or decreases in area along the z direction.

14. The imaging system of claim 12, wherein the rigid flux filter device includes a plurality of flux reducing elements with a plurality of shapes having an invariant cross section along the z direction over a z-range larger than an extension of an x-ray beam in the z-direction.

15. A method, comprising:
rotating an x-ray radiation source about an examination region, wherein the x-ray radiation source emits x-ray radiation that traverses the examination region;
filtering the x-ray radiation that traverses the examination region with a rigid flux filter device, wherein the rigid flux filter device is disposed in the examination region and does not rotate together with the x-ray radiation source, wherein along an axis direction around which the x-ray radiation source rotates, the rigid flux filter device is configured to slide, relative to the examination region, toward the examination region from a location at which the rigid flux filter device is spaced apart from the examination region in the axis direction; and
detecting, with detector pixels located opposite the x-ray radiation source, across from the examination region, x-ray radiation traversing the flux filter device and generating a signal indicative thereof.

16. The method of claim 15, wherein the rigid flux filter device includes an inner region with first attenuation characteristics, a first outer region with second attenuation characteristics, and a second outer region,
wherein the inner region is disposed between the first and second outer regions in a plan view, and
wherein the inner region that is disposed between the first and second outer regions in the plan view attenuates the x-ray radiation to a greater degree than each of the first and second outer regions.

* * * * *